United States Patent
Silpe (10) Patent No.: US 9,068,695 B2
(45) Date of Patent: Jun. 30, 2015

(54) ACTIVE GUIDANCE OF FLUID AGENTS USING MAGNETORHEOLOGICAL ANTIBUBBLES

(75) Inventor: Justin E. Silpe, Princeton, NJ (US)

(73) Assignee: SMRT Delivery LLC, Birmingham, MI (US)

( * ) Notice: Subject to any disclaimer, the term of this patent is extended or adjusted under 35 U.S.C. 154(b) by 318 days.

(21) Appl. No.: 13/592,546

(22) Filed: Aug. 23, 2012

(65) Prior Publication Data
US 2013/0327409 A1 Dec. 12, 2013

Related U.S. Application Data

(60) Provisional application No. 61/658,659, filed on Jun. 12, 2012.

(51) Int. Cl.
F17D 1/08 (2006.01)
F17D 1/00 (2006.01)

(52) U.S. Cl.
CPC ............ *F17D 1/00* (2013.01); *Y10T 137/0391* (2015.04)

(58) Field of Classification Search
CPC ......................................................... F17D 1/00
USPC ............................ 137/13, 827, 909; 210/222
See application file for complete search history.

(56) References Cited

U.S. PATENT DOCUMENTS

| | | | |
|---|---|---|---|
| 3,485,758 A | | 12/1969 | Borrows |
| 3,805,272 A | * | 4/1974 | Fan et al. ..................... 347/53 |
| 3,916,419 A | * | 10/1975 | Fan et al. ..................... 347/55 |
| 4,388,593 A | | 6/1983 | Mittleman |
| 4,726,914 A | * | 2/1988 | Fellows et al. ............... 252/392 |
| 4,963,883 A | * | 10/1990 | Matsui .......................... 347/48 |
| 5,541,072 A | * | 7/1996 | Wang et al. ................. 435/7.21 |
| 5,594,179 A | * | 1/1997 | Marsh ........................ 73/861.07 |
| 5,777,649 A | * | 7/1998 | Otsuka et al. ................. 347/94 |
| 6,120,133 A | * | 9/2000 | Ahn ............................. 347/53 |
| 6,416,740 B1 | * | 7/2002 | Unger ......................... 424/9.52 |
| 7,204,581 B2 | * | 4/2007 | Peeters ......................... 347/53 |
| 7,263,825 B1 | * | 9/2007 | Wills et al. ..................... 60/295 |
| 8,372,658 B2 | | 2/2013 | Shikida et al. |

(Continued)

FOREIGN PATENT DOCUMENTS

WO  WO 2005069015 A1 *  7/2005  ............. G01N 35/10

OTHER PUBLICATIONS

Dorbolo, S. et al., Fluid Instabilities in the Birth and Death of Antibubbles, *New Journal of Physics* 5: 161, 2003.

(Continued)

*Primary Examiner* — Craig Schneider
*Assistant Examiner* — Minh Le
(74) *Attorney, Agent, or Firm* — Gifford, Krass, Sprinkle, Anderson & Citkowski, P.C.

(57) ABSTRACT

Magnetorheological (MR) antibubbles are used for fluid delivery. A method of transporting a substance in a fluid in accordance with the invention comprising the steps of forming an antibubble in the fluid, the antibubble containing the substance to be transported and magnetic or magnetizable particles, and guiding the antibubble through the fluid with a magnet. The particles are ferromagnetic, paramagnetic or diamagnetic, and the magnet is a permanent magnet or an electromagnet. The substance to be transported may include a reactant associated with a catalytic mechanism; a pigment; or a lubricant. The delivery system may include a substance or magnetic particles which are fluorescent.

14 Claims, 4 Drawing Sheets

(56) References Cited

U.S. PATENT DOCUMENTS

| | | |
|---|---|---|
| 2001/0022151 A1* | 9/2001 | Sliwinski et al. ............. 106/453 |
| 2003/0096419 A1* | 5/2003 | Trigiani .......................... 436/56 |
| 2005/0084800 A1* | 4/2005 | Tawa ........................ 430/270.11 |
| 2005/0109410 A1* | 5/2005 | Gilbert et al. ................. 137/827 |
| 2006/0037657 A1* | 2/2006 | Shibata et al. ................ 137/827 |
| 2007/0063167 A1* | 3/2007 | Cheng et al. ............... 252/62.52 |
| 2008/0245430 A1* | 10/2008 | Adleman et al. .............. 137/827 |
| 2008/0257823 A1* | 10/2008 | Martikainen ................. 210/660 |
| 2009/0090422 A1* | 4/2009 | Baroud et al. ................ 137/827 |
| 2009/0117664 A1* | 5/2009 | Shinoda ........................ 436/172 |
| 2009/0235990 A1* | 9/2009 | Beer ................................ 137/3 |
| 2009/0308473 A1* | 12/2009 | Shinoda ........................ 137/827 |
| 2010/0068764 A1* | 3/2010 | Sista et al. ...................... 435/79 |
| 2010/0108311 A1* | 5/2010 | Daussin et al. .......... 166/250.01 |
| 2010/0139797 A1* | 6/2010 | Delamarche .................. 137/806 |
| 2010/0259584 A1 | 10/2010 | Hawkins et al. |

OTHER PUBLICATIONS

Kim, P. et al., Dynamics of the Formation of Antibubbles, *Europhysics Letters* 83: 54001, 2008.

Silpe, J. et al., Magnetic Antibubbles: Formation and Control of Magnetic Macroemulsions for Fluid Transport Applications, *Journal of Applied Physics* 113 (17B304), 2013.

Silpe, J. et al., Generation of Antibubbles from Core-Shell Double Emulsion Templates Produced by Microfluidics, *Langmuir* 29: 8782-87, 2013.

* cited by examiner

ACTIVE GUIDANCE OF FLUID AGENTS USING MAGNETORHEOLOGICAL ANTIBUBBLES

REFERENCE TO RELATED APPLICATION

This application claims priority from U.S. Provisional Patent Application Ser. No. 61/658,659, filed Jun. 12, 2012, the entire content of which is incorporated herein by reference.

FIELD OF THE INVENTION

The present disclosure relates generally to fluid transport phenomena. More particularly, the present invention relates to apparatus and methods for actively guiding fluids by way of magnetorheological (MR) antibubbles.

BACKGROUND OF THE INVENTION

Splashing, via the impact of a liquid or solid upon a fluid surface, can lead to air entrainment, which, in the presence of a surfactant, produces stable and metastable bubbles [1,2]. The most familiar of these is the soap bubble, a structure in which a thin film of liquid separates the air inside from the air outside the bubble. Equally common, yet widely unrecognized, is the antibubble, so called for its reverse phase construction, wherein a thin layer of air separates two liquids [2,3]. Although first observed nearly eight decades ago [4], and coined only in the last four [5], antibubbles remain a relatively late-breaking phenomenon.

Despite their initial account, antibubbles have since realized no immediate application, and thus, insofar as is known, practical uses for such bubbles do not exist. In contrast to antibubbles, fluid transport systems have been in use for years. Typically, these transport systems are employed in industries of pharmaceutical, petrochemical, and organic chemical synthesis, most expansively, by way of conduits. Nonetheless, previous attention paid in these fields has thus far failed to consider the possible use of, herein described, magnetic antibubble technology.

Numerous industrial systems, from lubrication to froth flotation necessitate a thorough understanding of the impact (both physically and figuratively) of liquids at liquid and solid interfaces [1,2]. The main problem with conventional guided fluid transport systems is that there is no way to target a specific liquid to a specific location. In addition, while the conventional guided fluid transport systems are that while they can be enclosed in a time-release capsule, liquid substances themselves can be dispersed neither on demand nor at an isolated location and time.

SUMMARY OF THE INVENTION

In broad and general terms, this invention exploits magnetorheological (MR) antibubbles for fluid delivery. The various embodiments depart substantially from conventional concepts and designs associated with prior delivery systems, and in so doing provide apparatus and methods applicable to organic chemical transportation, reaction, delivery and/or distribution. The MR antibubble device has many of the advantages of the liquid delivery systems mentioned heretofore and many novel features that result in a unique delivery method for actively guiding fluids.

A method of transporting a substance in a fluid in accordance with the invention comprising the steps of forming an antibubble in the fluid, the antibubble containing the substance to be transported and magnetic or magnetizable particles, and guiding the antibubble through the fluid with a magnet. The particles are ferromagnetic, paramagnetic or diamagnetic, and the magnet is a permanent magnet or an electromagnet. The substance to be transported may include a reactant associated with a catalytic or corrosion mechanism; a pigment; or a lubricant. The trasnsport system may include a substance or magnetic particles which are fluorescent.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

This invention exploits magnetorheological (MR) antibubbles for fluid delivery. To achieve this, the present invention generally comprises an applied magnetic field and source thereof (e.g. an electromagnet), used to effect the MR antibubble's path and orientation; a continuous phase, consisting, minimally, of an aqueous or organic liquid (or emulsion, suspension, or solution thereof), used to suspend the MR antibibbles; a vessel, used to hold the continuous phase and contained MR antibubbles; and a dispersed phase, consisting, minimally, of an aqueous or organic liquid, supplemented with a surface tension reducing agent and magnetic particles of variable size and concentration. Note as used herein, an "organic" liquid may be taken to mean any non-aqueous fluid applicable to the invention including, but not limited to oils, gels, waxes, and so forth.

Figure 1:
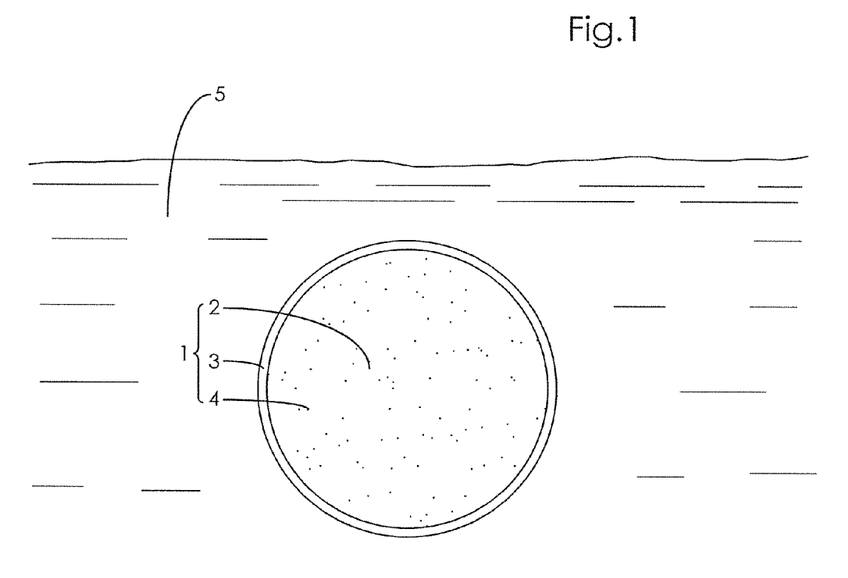
FIG. 1 is an illustration of the MR antibubble itself.
Figure 2:
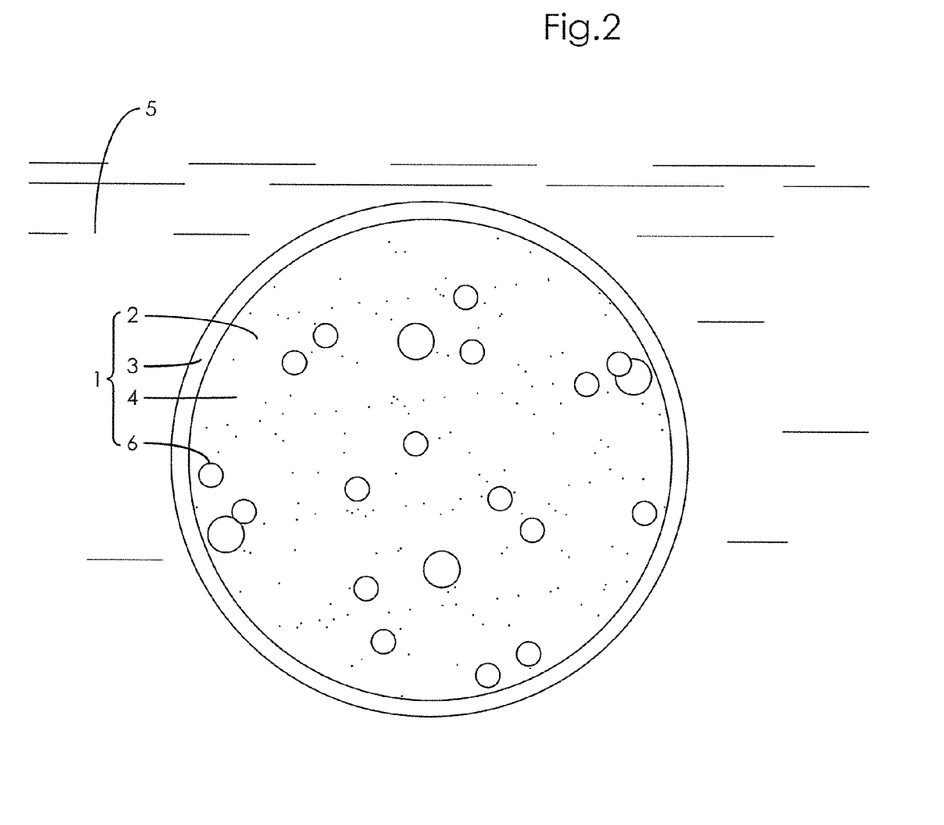
FIG. 2 is an illustration of a MR antibubble subjected to higher magnifications. The black particles represent the iron oxide, while the internal spheres represent the capability of the antibubble to possess a desired fluid.

The MR antibubble itself, 1, shown in FIG. 1, includes a thin spherical, gaseous layer 3 encapsulating a liquid (the "dispersed phase" 2) in which magnetic or magnetizable particles 4 are suspended. The antibubble is suspended in a surrounding aqueous or organic medium (the "continuous phase" 5). FIG. 2 is an illustration of a MR antibubble subjected to higher magnifications. The black particles 4 represent iron oxide, while the internal spheres 6 represent the capability of the antibubble to possess a desired fluid.

The mechanism by which an antibubble forms is vaguely reminiscent of blowing conventional soap bubbles in that it too entails a deformation of the surface [2], however, in the case of antibubbles, this occurs with a liquid rather than air. Briefly, MR antibubbles are formed when a liquid column, i.e., a fluidic jet of dispersed phase (that which must also comprise the magnetic component), is injected into a bath of continuous phase. At this interface, the liquid jet impacts the continuous phase boundary in such a way so as to effect a thin film of air be entrained between the two liquids (beneath the surface) [2]. Advection near the jet exit forces the trailing end of the liquid column to adopt a thinning neck. Due to Rayleigh-Plateau instability, the jet neck eventually breaks, pinching-off from the surface to form a liquid pocket surrounded by a shell of gas: a MR antibubble. In order for a conventional antibubble to be considered or regarded as "magnetorheological", it must encapsulate a small fraction of magnetic material.

Figure 4:
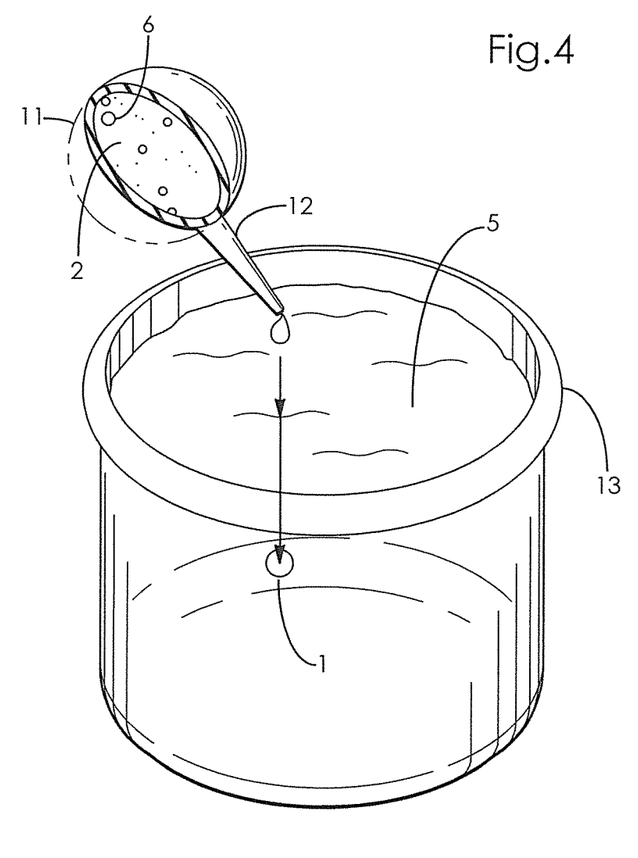
FIG. 4 is an illustration of the formation of the MR antibubble.

The vessel 13 is used to contain the continuous phase as well to suspend the MR antibubble. The dispersed phase, as previously noted, is made from a mixture that must contain, but is not limited to, a surface tension reducing agent and an aqueous or organic liquid. Additionally, and in accordance with the invention, the magnetic component must be incorporated into the dispersed phase (and at a minimally sufficient concentration) such that it confers the resultant antibubbles' magnetorheological character, responsible for their controlled delivery. Depending on the size and intrinsic solubility of the magnetic particles used, the dispersed phase may itself constitute a biphasic system, delineated, only broadly, by the carrier fluid and suspended magnetic particles. As shown in FIG. 4, a squeeze bulb 11 with nozzle 12 may be used to house the dispersed phase prior to antibubble formation.

For the experiments leading up to the present invention and effect of MR antibubbles, a parallelepiped glass vessel was employed. The vessel is filled with the continuous phase prior to antibubble formation and is exposed at the top to allow for both its filling and subsequent antibubble formation. The dispersed phase was injected into the vessel of continuous phase, by way of fluidic jet (approximate initial diameter 3 mm), at volumes ranging from 0.2 mL-0.8 mL (yielding approximate bubble diameters between 5 mm-2 cm). All MR antibubbles were created at 25° C., with initial velocities and drop heights less than 24 cm/s and in the range of 8-18 mm, respectively. This is in line with previously published results [2] on the dynamics of classic (nonmagnetic) antibubble formation and specifications thereof. Furthermore, to eliminate transient spikes in the potential difference between the two liquids, a 20 µF capacitor was retained. AC shorting the phases prevents the potential difference from exceeding a critical formation threshold to a similar end as DC shorting in [3].

Briefly, the wire is secured at one end in the lumen of the squeeze bulb (housing the dispersed phase) and extends outwardly through a small protrusion in the bulb wall to ensure simultaneous contact between the two phases and the copper wire at the time of antibubble formation. The MR antibubbles thus produced had diameters in the rage of 5 mm-2 cm and average lifetimes of approximately 200 seconds (assuming no magnetically induced popping). The continuous phase was prepared by mixing 200 mL of 99% pure glycerol with 2.8 L of deionized water and adding 15 mL (0.5% v/v) of Dawn 0 Ultra Concentrated dishwashing soap. In order to make the dispersed phase, an aliquot of continuous phase was taken and supplemented with $Fe_3O_4$ powder (average particle diameter 30 µm). Due to the inherently high density and limited solubility of $Fe_3O_4$, the dispersed phase precipitates over time, and thus, the $Fe_3O_4$ content of a typical MR antibubble can only be approximated to high µM/low mM concentrations.

Thus formed, MR antibubbles exhibit novel fluid transport in the presence of an externally applied magnetic field. At a given critical intensity, the imposed magnetic field leads to a mismatch in the normal stress condition at the air layer interface; the $Fe_3O_4$ particles, from which the magnetic forces originate, attempt to slip relative to the surrounding phase and thereby transmit drag to the fluid, causing the dispersion to behave largely as a whole [6]. In this way, the behavior of the antibubble may be described as an ensuing competition between the surface energy of the air layer to favor its spherical geometry and the magnetic potential energy of the magnetic particles to reduce their separation from the magnetic source [6]. In a relatively low intensity magnetic field, the pressure exerted on the interfacial air layer by the $Fe_3O_4$ is sufficient to effect rigid motion (i.e., translation) of the antibubble without significant deformation. This, we observe macroscopically in the form of movement towards the magnet. Upon the application of a higher intensity magnetic field (or by closer approach to the source of a nonuniform magnetic field), however, the pressure exerted at the interface too far exceeds the air layer's capacity to alleviate it, and thus the $Fe_3O_4$ accelerates through the boundary, rupturing the antibubble.

The magnetic antibubbles we have herein sought to describe make use of an internal phase composed, namely, of $Fe_3O_4$ to enable their control in the presence of a single external magnetic field. It is therefore a critical systems requirement that we be able to discern transport control (i.e., movement) from fate control (i.e., release, rupture). To this end, we characterize the general behavior of the magnetic antibubbles in terms of three broad factors influencing their kinematics: the intensity of the magnetic field, the concentration of $Fe_3O_4$ in the dispersed phase, and the various other fluid properties (e.g., buoyancy, drag) of the system. If $Fe_3O_4$ concentration and "various other fluid properties" are kept constant, we find the controllability of the antibubble to be solely maintained by the gradient magnetic field, the intensity of which exponentially decays with distance from the magnetic source.

The buoyancy force creates a rising tendency and can be described by $$F_b = (\rho_1 - \rho_a) V_a g$$

where $\rho$ is the density of the continuous phase, $\rho_a$ is the net density of the antibubble, $V_a$ is the volume of the antibubble, and g is the gravitational acceleration constant. It is important to note that $p_a$ has a dependency with the concentration of ferromagnetic component. The drag force is correlated with the velocity of the antibubble, and hence is manipulated based on the magnitude and direction of the magnetic field. Although not described here, the drag force on bubble motion has been well characterized [7]. The magnetic force can be described by $$F_m = 1/2 \mu_o (\mu_f - \mu_1) V_i \gamma_f / \rho_f \nabla \|H(r,t)\|^2$$

where $\mu_o$ is the magnetic permeability of free space, $\mu_f$ is the permeability of the ferromagnetic component, $\mu_1$ is the permeability of the continuous phase, $V_i$ is the volume of the dispersed phase within the antibubble, $\gamma_f$ is the mass concentration, $\rho_f$ is the density of the ferromagnetic component, $\nabla$ is the gradient operator, $\|\|$ is the Euclidean norm, and H(r,t) is the applied magnetic field. For simplicity, it is assumed that the magnetic force acts at the center of mass of the antibubble. In the absence of disruptive flow, the movement of the antibubble sees contribution from each of the three aforementioned forces: buoyant, drag, and magnetic. Therefore, creating complex and transient magnetic fields through electromagnet arrays can offer active transport and delivery of multifunctional dispersed phases. Similar systems using feedback control have been developed for magnetic particle guidance [8].

Regarding utility, MR antibubbles are generated with desired fluid(s) and/or agents, and a source of magnetism, used to direct the antibubbles to a desired site where the fluid can then be dispersed and ultimately utilized. One application of such an approach pertains to synthetic organic chemistry, specifically, heterogeneous catalytic processes.

Catalytic reactions are of tremendous importance in both industrial and laboratory applications [9,10]. Heterogeneous catalysts often require rare and expensive metals, and their conservation should therefore be sought out. The chemical reactions of heterogeneous catalysis occur between compounds adsorbed on the surface of the solid catalyst. The entire cycle comprises five consecutive steps [9], each of which can have more or less influence on the overall reaction rate, depending on its relation to the others. The steps are:

(1) diffusion of the reacting substances over the catalyst particle [9];

(2) adsorption of the reacting substances on the catalyst [9];

(3) interaction of the reacting substances on the surface of the catalyst [9];

(4) desorption of the reaction products from the catalyst particle [9];

(5) diffusion of the reaction products into the surrounding medium [9].

For reactions in which the observed rate is determined by the rate of surface reaction, the metallic area of the catalyst becomes the most important feature. Hence, it is important to make and stabilize the highest possible and most easily accessible metal surface area. Although finely divided metallic powders can be made with high surface areas, these are very unstable under most reaction conditions [9]. As such, supported metal catalysts are often necessitated. A supported metal is one that exists in the form of metal crystallites attached to the surface of a support. However, the high intrinsic activity and highly specific surface typically associated with supported metal catalysts are not in themselves sufficient. The reactants must also be able to reach the active surface quickly in order to undergo catalysis [9]. These movements of molecules through the fluid surrounding the solid catalyst are governed by the laws of diffusion (i.e., Fick's law) such that the flow of a molecule is proportional to its gradient of concentration and pressure.

In light of this diffusion-mediated process, the use of MR antibubbles, pre-loaded with reactants to a catalytic mechanism and guided by a magnetic source (whose field outlines the path to the catalytic surface), confers significant rate enhancements over conventional, diffusion-limited methods. The catalytic rate enhancement by this invention arises out of its magnetically endowed capacity to actively transport and deliver organic chemicals, via the MR antibubbles, to a catalytic site. Furthermore, because the MR antibubbles serve only to increase the local reactant concentration at the catalytic surface without any alteration in the inherent reaction mechanism, the invention assumes a wide-range of applicability among various reaction schemes of reactants and catalysts.

Another exemplary embodiment of MR antibubbles pertains to high quality inkjet printing, where the ability to accurately and precisely position liquid drops from fluid ejectors at predetermined locations is paramount. The controlled positioning of a drop, as determined from its ejection by the inkjet printhead, suffers from multiple sources of error. These tend to be a combination of at least two factors inherent to the current method: repeated placement errors, arising from permanently malformed printheads and unintended physical contact between residual debris and the printhead itself; and errors of a stochastic nature, in which the drop-to-drop variability in the contact point of the drop tail as it leaves the ejector surface affects random inconsistencies in drop positioning [11]. Also included in this is the unintended formation of satellite drops, produced by the unpredictable breakup or recombination of multiple drops as they travel to the receiver plate.

In both cases, the presence of disproportionately sized drops causes significant reduction in image quality due to fluid accumulation at undesirable regions. The formation of satellite drops can be controlled to some extent by adjusting the ink's physicochemical formulation. However, the typical modifications required to minimize satellite drops are often concomitant with an intrinsically suboptimal ink performance and, thus, quality is often too far compromised to appreciate any benefit to their absence.

Additional efforts to overcome these errors are generally limited to the effect of minimizing physical separation between printhead and receiver [11]. The magnitude of drop displacement scales with the distance parameter directly, insofar as the total displacement of a drop is equal to its average velocity multiplied by its duration through the ejector nozzle onto the receiver plate. By positioning the receiver in closer proximity (than what otherwise would be) to the printhead, drops that are angularly defective, have far less time to maintain their misguided trajectories before reaching the receiver plate [11]. The distance must be modulated, however, in that a closer spacing will increase the likelihood of mechanical contact between the printhead and receiver, resulting in a potentially malfunctioning ejector nozzle.

By filling and forming ink-filled MR antibubbles, and placing a high precision electromagnet beneath the receiver plate, the forgoing inaccuracies and imprecisions are addressed. With regard to the inherent drop-to-drop variability, in both velocity and size, in the prior art, the present invention is controlled by a mechanical pump/aspirator capable of ejecting a precise volume, accurate to 0.1 µL, of dispersed phase. At the printhead nozzle and upon its localization above the receiver, the MR antibubble will rupture, dispersing its ink at the desired point on the receiver plate by the precise electromagnetic field located just beneath. In this way, the control device of the present invention introduces a second means for accurate and precise drop positioning; in addition to the current state of the art, whereby the control device is centered at the drop source (printhead nozzle), the control device of the MR antibubble, by the electromagnetic field, is positioned remotely at the target site (receiver plate). The dual positioning system, from source-to-site, confers significant advantages in the regulation of drop trajectory and velocity throughout the printing process.

In a third exemplary embodiment, the present invention is a method for performing magnetic particle inspection (MPI) of ferrous structures in an underwater environment. Various metallographic techniques, the majority of which expand several forms of microscopy and X-ray diffraction, demonstrate the advancement and capacity in the materials science field to elucidate intricate microscopic features and qualities of most metals of industry. For the purposes of quality control and/or assurance, in cases where defective or flaw-containing products can be linked to lot-to-lot variability in their manufacture, these methods prove a vital test [12]. This, insofar as a high precision metallographic technique, when performed on a small portion of an otherwise large lot, can provide sufficient analytic data to characterize the rest of the (untested) lot as a whole. Employed for industrial applications, however, high precision testing is highly limited by the destructive nature inherent to the techniques. To this end, the value of non-destructive testing is evident in such cases where the specimen of interest is either already in service or of too great a value to destroy and replace.

MPI is a method of non-destructive testing for surface and subsurface flaws in ferrous materials. The process itself entails the induction of a magnetic field in a specimen of interest, applying a formulation (i.e., powder or liquid) of certain magnetic compounds to the specimen, and visually inspecting the surface for a differential coverage or cluster pattern of the magnetic compound [12]. MPI is employed most effectively, among industrial applications, in the detection of three commonly encountered classes of material defects: the most immediate of which is borne by the material's frequent use in service, manifested in the form of normal "wear-and-tear"; the second, conceived at the point of manufacture; and the third, more proximally by the inherent metallographic properties of the material itself [12,13]. While MPI and devices thereof have proven particularly well-suited for metallographic inspection procedures under conventional circumstances (i.e., gas (surrounding)-magnetic particle (powder or liquid) ferrous specimen (solid)), they have been found severely deficient for use by divers in testing structures in the underwater environment (i.e., liquid (surrounding)-magnetic particle (powder or liquid)-ferrous specimen (solid)) [14].

In this embodiment, one or more magnetic particles of the present invention are fluorescent. Such particles may be obtained according to [15], wherein finely divided iron oxides are mixed with fluorescent thermoplastic resin pigments to form water or oil suspensions of the like. The dispersed phase is then prepared with the addition of surfactant and aqueous or organic liquid, as outlined above. Upon sufficient irradiation (as defined by a well-characterized absorption/emission spectrum), excited fluorophores in the resultant mixture will fluoresce, and thus light need not be present for their detection. MR antibubbles, thus produced, may be formed in the underwater environment (i.e. the working environment of the specimen to be tested) in the vicinity of the test specimen surface. The fluorescent magnetic particles remain in suspension within the intact MR antibubbles until they are attracted and ultimately ruptured by the increasing magnetic field emanating from the magnetized specimen. The fluorescent magnetic particles, which are now mobile in the carrier fluid of the dispersed phase, will agglomerate near the fringing magnetic field of a surface defect and accumulate with the magnetization of the specimen. The inspection itself is executed in a similar fashion as conventional (and other underwater) MPI, and is thus a familiar technique to those skilled in the art.

Additional Considerations.

There has thus been outlined, rather broadly, the preferred embodiments of the present invention in order that a working understanding of the device and methods be gained, and in order that the present contribution to the art may be better appreciated. In this respect, it is to be understood that the invention is not limited in its application to the details of construction and to the arrangements of the components set forth in the description. Also, it is to be understood that the phraseology and terminology employed herein are for the purpose of the disclosure and should not be regarded as limiting.

There are additional considerations regarding the present method such that it is capable of other embodiments and of being practiced and carried out in various ways. These additional considerations include: (1) the air layer encapsulating the MR antibubble may be substituted for various other gases (e.g., argon, nitrogen, sulfur hexafluoride) on the basis of inertness, density, and/or solubility; (2) the magnetic component may consist of materials having discrete ferromagnetic qualities (e.g., $\gamma\text{-}Fe_2O_3$), ferrimagnetic qualities (e.g., $Fe_3O_4$), or any such combination of the two. Furthermore, the magnetic component can be mixed and continually resuspended in the dispersed phase, or it can be incorporated by more advanced methods into the surfactant itself [16]; (3) strongly diamagnetic material (e.g., pyrolytic carbon, bismuth) may be substituted for the magnetic component of the present invention in preparation of the MR dispersed phase and MR antibubbles thereof. Formed in this fashion, diamagnetic MR antibubbles produce an opposing magnetization relative to the externally applied magnetic field of the present invention. As such, MR antibubbles can be guided either by repulsion (diamagnetically), or attraction (ferromagnetically or ferrimagnetically), depending on the material used.

Figure 3:
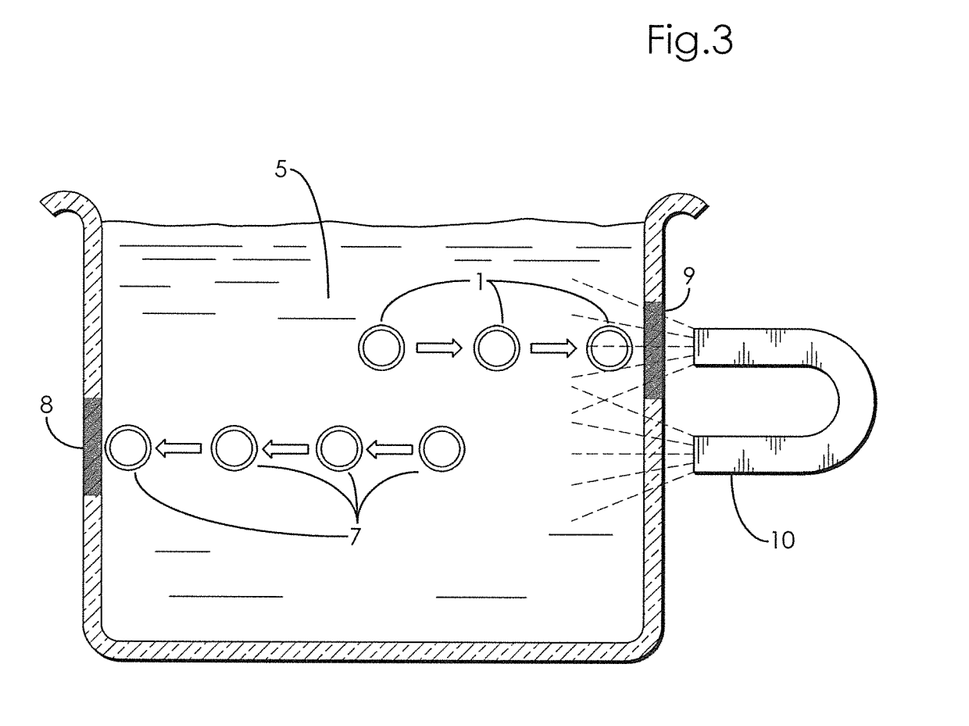
FIG. 3 is an illustration of the antibubble's magnetorheological qualities as it is compelled toward a permanent magnet.

With regard to FIG. 3, in which there is a ferromagnetic MR antibubble 1, a diamagnetic MR antibubble 7, two desired sites 8, 9 located left and right, respectively, within the continuous phase 5, and a source of an externally applied magnetic field 10. In this drawing, antibubble 1 proceeds to site 9 by attraction to 10 disposed behind 9. On the other hand, diamagnetic MR antibubble 7 proceeds to site 8 by repulsion from field 10. Thus, 10 may remain behind 9 and yet still effectively guide 7 to 8.

REFERENCES

[1] Frohn A, Roth N. Dynamics of droplets. Springer Verlag; 2000.
[2] Kim P G, Stone H A. Dynamics of the formation of antibubbles. Eur Lett 2008; 83:54001.
[3] Dorbolo S, Caps H, Vandewalle N. Fluid instabilities in the birth and death of antibubbles. New J Phys 2003; 5:161.
[4] Hughes W, Hughes A R. Liquid Drops on the Same Liquid Surface. Nature 1932; 129:59.
[5] Strong C L. The amateur scientist: Curious bubbles in which a gas encloses a liquid instead of the other way around. Sci Am 1974; 230:116-20.
[6] Bacri J C, Salin D, Massart R. Study of the deformation of ferrofluid droplets in a magnetic field. J Phys Lettres 1982; 43:179-84.
[7] Malysa K, Krasowska M, Krzan M. Influence of surface active substances on bubble motion and collision with various interfaces. Adv Colloid Interface Sci 2005; 114-115: 205-25.
[8] Ruuge E K, Rusetski A N. Magnetic fluids as drug carriers: Targeted transport of drugs by a magnetic field. J Magn Magn Mater 1993; 122:335-9.
[9] Le Page J F. Applied heterogeneous catalysis: Design, manufacture, and use of solid catalysts. Editions Technip; 1987.
[10] Crocker M J. Handbook of acoustics. Wiley-Interscience; 1998.
[11] Hawkins G A, Gao Z, Xie Y, Furlani E P, Ng K C. Microfluidic device for controlling direction of fluid. U.S. Patent WO/2010/117428, 2010.
[12] Doane F B. Principles of magnaflux inspection. Photopress, Inc.; 1940.
[13] Southwest Research Institute. Nondestructive testing: A survey. Technology Utilization Office, National Aeronautics and Space Administration; 1973.
[14] Mittleman J. Coil device for underwater magnetic testing. U.S. Pat. No. 4,388,593, 1983.
[15] Borrows PK. Method of making fluorescent magnetic particles. U.S. Pat. No. 3,485,758, 1969.
[16] Brown P, Bushmelev A, Butts C P, Cheng J, Eastoe J, Grillo I, et al. Magnetic control over liquid surface properties with responsive surfactants. Angew Chem Int Ed 2012; 51:2414-6.

The invention claimed is:

1. A method of transporting a substance in a fluid, comprising the steps of:
    forming an antibubble in the fluid, the antibubble including a thin, generally spherical gaseous layer encapsulating a liquid;
    the encapsulated liquid containing a substance to be transported and magnetic or magnetizable particles; and
    guiding the antibubble through the fluid with a magnet using attraction or repulsion between the magnet and the magnetic or magnetizable particles.

2. The method of claim 1, wherein the particles are ferromagnetic, paramagnetic or diamagnetic.

3. The method of claim 1, wherein the magnet is a permanent magnet or an electromagnet.

4. The method of claim 1, wherein the substance to be transported includes a reactant associated with a catalytic mechanism.

5. The method of claim 1, wherein the substance to be transported includes a pigment.

6. The method of claim 1, wherein the substance to be transported includes a lubricant.

7. The method of claim 1, wherein the substance to be transported includes a corrosion inhibitor.

8. The method of claim 1, wherein the substance to be transported promotes wastewater treatment.

9. The method of claim 1, including a substance or magnetic particles which are fluorescent.

10. The method of claim 1, wherein the gaseous layer is air.

11. The method of claim 1, wherein the gaseous layer is argon.

12. The method of claim 1, wherein the gaseous layer is nitrogen.

13. The method of claim 1, wherein the gaseous layer is sulfur hexafluoride.

14. An antibubble formed in accordance with the method of claim 1.

* * * * *